US00PP19450P3

(12) United States Plant Patent
Freyre

(10) Patent No.: US PP19,450 P3
(45) Date of Patent: Nov. 18, 2008

(54) ***NOLANA HYBRIDA* CULTIVAR 'LORMA BLANCA'**

(50) Latin Name: *Nolana hybrida*
Varietal Denomination: Loma Blanca

(75) Inventor: Rosanna Freyre, Gainsville, FL (US)

(73) Assignee: University of New Hampshire

( * ) Notice: Subject to any disclaimer, the term of this patent is extended or adjusted under 35 U.S.C. 154(b) by 98 days.

(21) Appl. No.: 11/646,861

(22) Filed: Dec. 28, 2006

(65) Prior Publication Data

US 2008/0184422 P1 Jul. 31, 2008

(51) Int. Cl.
*A01H 5/00* (2006.01)

(52) U.S. Cl. ..... Plt./263.1

(58) Field of Classification Search ..... None
See application file for complete search history.

(56) References Cited

U.S. PATENT DOCUMENTS

PP14,141 P2 * 9/2003 Godard ..... Plt./263.1

* cited by examiner

*Primary Examiner*—Wendy C. Haas
(74) *Attorney, Agent, or Firm*—Devine, Millimet & Branch; Paul C. Remus; Raymond I. Bruttomesso, Jr.

(57) ABSTRACT

A new and distinct cultivar of *Nolana* plant named 'Loma Blanca', characterized by numerous single flowers that are white in color with a dark purple veined center; dark purple anthers and pollen grains, freely branching growth habit, no fruit set from self pollination, and good performance in the garden and as a hanging basket.

2 Drawing Sheets

Botanical designation: *Nolana hybrida.*
Variety denomination: 'Loma Blanca'.

BACKGROUND OF THE INVENTION

The present Invention relates to a new and distinct cultivar of *Nolana* plant, botanically known as a *Nolana* artificial hybrid, and hereinafter referred to by the cultivar name 'Loma Blanca'.

The new *Nolana* is a product of a planned breeding program conducted by the Inventor in Durham, N.H. The objective of the breeding program is to create new compact *Nolana* plants with attractive flowers, profuse flowering and reduced fruit set.

The new 'Loma Blanca' originated from seed collected from open pollination of a proprietary selection of *Nolana* identified with code number UNH N2-46-2 (NOL5), not patented. Seed was collected from a greenhouse-grown plant on Jan. 17, 2003 and sown on Nov. 24, 2003. From the progeny, a single plant N5-OP-24 was selected in Durham, N.H., USA, on the basis of its profuse flowering, compact growth habit and attractive flowers.

Asexual reproduction of the new cultivar by terminal vegetative cuttings since April, 2004, taken in Durham, N.H. has shown that the unique features of this new *Nolana* are stable and reproduced true to type in successive generations.

SUMMARY OF THE INVENTION

Plants of the cultivar 'Loma Blanca' have not been observed under all possible environmental conditions. The phenotype may vary somewhat with variations in environment such as temperature, light intensity and day length without, however, any variance in genotype.

The following traits have been repeatedly observed and are determined to be the unique characteristics of 'Loma Blanca'. These characteristics in combination distinguish 'Loma Blanca' as a new and distinct cultivar:

1. Numerous single flowers that are white in color with a dark purple veined center.
2. Dark purple anthers and pollen grains.
3. Freely branching growth habit.
4. No fruit set from self pollination.
5. Good performance in the garden and as a hanging basket.

In side-by-side comparisons conducted in Durham, N.H., plants of the new *Nolana* differed from plants of the parent selection, in the following characteristics:

1. Flowers of plants of the new *Nolana* were white with dark purple center while flowers on the parent selection were light blue with white center.
2. Flowers of plants of the new *Nolana* had dark purple anthers and pollen grains while flowers on the parent selection were white.
3. Plants on the new *Nolana* were less pubescent than plants of the parent selection.

Plants of the new *Nolana* can be compared to plants of *Nolana* cultivar 'Nolgold' (a.k.a. 'Blue Eyes') U.S. Plant Pat. No. 14,141. In side-by-side comparisons conducted in Durham, N.H., plants of the new *Nolana* differed from plants of 'Nolgold' in the following characteristics:

1. Plants of the new *Nolana* had white flowers with purple center while flowers on the cultivar 'Nolgold' were blue violet and white bicolored.
2. Flowers of plants of the new *Nolana* had dark purple anthers and pollen grains while flowers on the cultivar 'Nolgold' were white.
3. Plants of the new *Nolana* had smaller flowers than plants of the cultivar 'Nolgold'.
4. Plants of the new *Nolana* had shorter internodes than plants of the cultivar 'Nolgold'.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Nolana.*

One photograph comprises a side perspective view of one typical 22-cm container of 'Loma Blanca' with three plants.

The other photograph is a close-up view of typical flowers and leaves of 'Loma Blanca'.

DETAILED BOTANICAL DESCRIPTION

The aforementioned photographs and following observations and measurements describe plants grown in Durham, N.H., in a heated greenhouse with 21° C. day/18° C. night set points. After planting rooted cuttings, plants were grown for about four months in 20-cm containers with three plants per container. Color references are made to The Royal Horticultural Society Colour Chart, 1995 Edition, except where general terms of ordinary dictionary significance are used. Color was evaluated under indirect, natural light.

Botanical classification: *Nolana* hybrid cultivar 'Loma Blanca'.

Parentage:

*Female parent.*—Proprietary selection of *Nolana* identified with code number UNH N2-46-2 (NOL5), not patented. UNH N2-46-2 (NOL5) was obtained from hybridization performed by the Inventor on Aug. 31, 2001, between a non-identified plant of *Nolana paradoxa,* and a non-identified plant of *Nolana aplocaryoides.*

*Male parent.*—Unidentified, seed was obtained from open pollination in a greenhouse containing multiple *Nolana* plants.

Propagation:

*Type cutting.*—Terminal vegetative cuttings.

*Time to initiate roots.*—About seven days at 21° C.

*Time to develop roots.*—About 15 days at 21° C.

*Root description.*—Fine, fibrous; white, color 155D.

*Rooting habit.*—Freely branching.

Plant description:

*Form.*—Annual flowering plant; moderately vigorous; outwardly spreading and trailing plant habit; uniformly mounded plant form. Freely branching habit with lateral branches potentially forming at very node.

*Plant height.*—About 30 cm.

*Plant diameter* (*area of spread*), *single plant.*—About 30 cm.

*Vigor.*—Moderately vigorous.

*Lateral branches.*—Length: About 15 cm. Diameter: About 2.5 mm. Internode length: 2–2.5 cm. Texture: glabrous. Color: 144B.

*Foliage description.*—Arrangement: alternate. Length: About 4 cm. Width: About 1 cm. Shape: elliptic. Apex: Acute. Base: Attenuate. Margin: Entire. Texture, upper and lower surfaces: Bullate surface, mostly glabrous with a few hairs on midrib. Venation pattern: Pinnate. Color: Developing leaves, upper and lower surfaces: 137B. Fully expanded leaves, upper surface: 137B. Fully expanded leaves, lower surface: 137C. Venation, upper and lower surfaces: 144A.

Flower description:

*Flower type and habit.*—Trumpet-shaped; single, axillary. Flowers face mostly upward or outward and are held above the foliage. Flowers not fragrant. Very freely flowering, typically about three open flowers and ten flower buds per lateral branch at one time.

*Natural flowering season.*—Plants flower from April to October in the Northern Hemisphere until frost in the autumn; flowering continuous during this period. Plants will flower under short or long days in a greenhouse.

*Flower longevity on the plant.*—About three days.

*Fragrance.*—None detected.

*Flower size.*—Diameter: 2.5–3 cm. Depth (height): 2.5–3 cm.

*Flower buds* (*showing color*).—Length: About 1 cm. Diameter: About 5 mm. Shape: Ovoid. Color: 94C.

*Petals.*—Quantity/arrangement: Five petals arranged in a single whorl, fused into a flared trumpet. Petal length from throat: About 2 cm. Petal width: About 1.3 cm. Shape: Funnel. Apex: Wavy. Base: United. Margin: Wavy. Texture, upper and lower surfaces: Smooth, satiny. Color: When opening, upper surface: 94D. When opening, lower surface: 91B. Fully opened, upper surface: 94D; upper base, 86A. Fully opened, lower surface: 91C; lower base, 145C.

*Sepals.*—Arrangement/appearance: Five sepals arranged in a single whorl; three sepals and two sepals fused together at the base. Length: About 1 cm. Width: About 2–3 mm. Shape: ovate. Apex: Acute. Base: Rounded. Margin: Entire. Texture, upper and lower surfaces: Smooth, glabrous. Color, upper and lower surfaces: 144A.

*Pedicels.*—Length: About 2 cm. Width: About 1 mm. Angle: About 45° from the main stem. Strength: Moderately strong. Texture: Smooth, glabrous. Color: 145A.

*Reproductive organs.*—Stamens: Quantity per flower: Five, adnate to base of the corolla tube. Anther shape: Elliptic. Anther length: About 1 mm. Anther width: About 1 mm. Anther color: 83C. Pollen amount: Abundant. Pollen color: 98B. Attachment to filament: dorifixed and versatile. Filament length: three short, about 5 mm; two long, about 8 mm. Filament width: About 1 mm. Pistils: Quantity per flower: One. Pistil length: About 1 cm. Style length: About 8 mm. Style color: 145C. Stigma shape: Oval. Stigma color: 144A. Ovary color: 145B.

*Seed/fruit.*—Seed and/or fruit production is moderate under open pollination with other *Nolana* plants. No seed and/or fruit production from self-pollination.

Disease/pest resistance: Plants of the new *Nolana* have not been noted to be resistant to pathogens or pests common to *Nolana.*

What is claimed is:

1. A new and distinct cultivar of *Nolana* plant named 'Loma Blanca,' as illustrated and described.

* * * * *

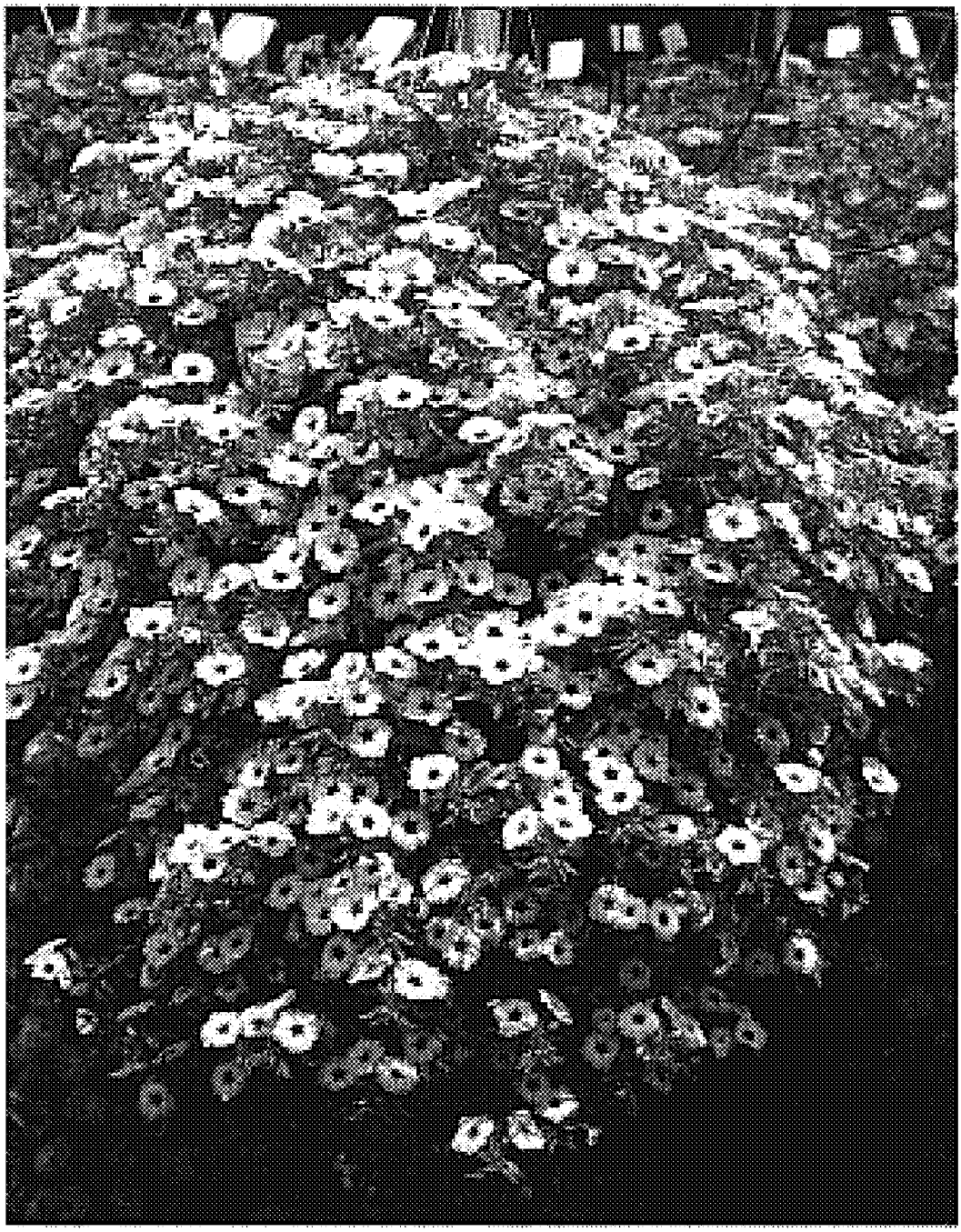

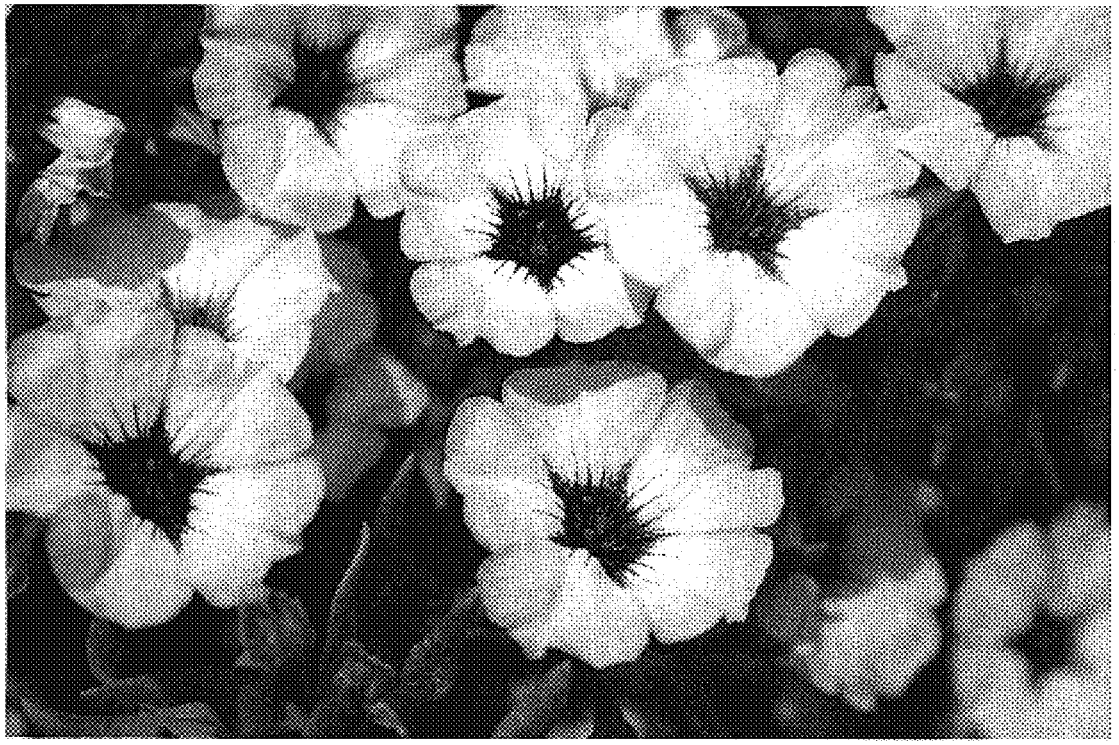

UNITED STATES PATENT AND TRADEMARK OFFICE

CERTIFICATE OF CORRECTION

PATENT NO. : PP 19,450 P3
APPLICATION NO. : 11/646861
DATED : November 18, 2008
INVENTOR(S) : Rosanna Freyre It is certified that error appears in the above-identified patent and that said Letters Patent is hereby corrected as shown below:

Title Pg, Item (54) Title:
Replace "Lorma Blanca" with -- Loma Blanca --.

Signed and Sealed this

Twenty-fourth Day of March, 2009

JOHN DOLL
*Acting Director of the United States Patent and Trademark Office*